United States Patent [19]
Marco et al.

[11] Patent Number: 5,849,064
[45] Date of Patent: Dec. 15, 1998

[54] SYSTEM AND METHOD FOR EVENLY SUSPENDING AND CIRCULATING PARTICLES IN A LIQUID

[75] Inventors: William P. Marco, Norcross; John M. Ward, Grayson; James P. Olivier, Lawrenceville; Preston P. Hendrix, Hoschton, all of Ga.

[73] Assignee: Micromeritics Instrument Corporation, Norcross, Ga.

[21] Appl. No.: 839,502

[22] Filed: Apr. 14, 1997

[51] Int. Cl.⁶ .................................................. B01D 19/00
[52] U.S. Cl. .............................. 95/30; 95/260; 95/262; 96/175; 96/204; 96/220; 96/389
[58] Field of Search ..................... 95/30, 260, 262; 96/175, 204, 206, 220, 228, 389; 210/533–535, 539, 409; 55/277, 242

[56] References Cited

U.S. PATENT DOCUMENTS

| | | | |
|---|---|---|---|
| 1,069,040 | 7/1913 | Stever | 210/534 |
| 3,229,448 | 1/1966 | Jacke | 96/175 |
| 3,614,434 | 10/1971 | Horwitz et al. | 250/364 |
| 3,787,185 | 1/1974 | Rohrbaugh et al. | 422/64 |
| 3,814,582 | 6/1974 | Rohrbaugh et al. | 436/43 |
| 3,853,500 | 12/1974 | Gassmann et al. | 95/30 |
| 3,879,129 | 4/1975 | Inoue | 250/564 X |
| 3,990,795 | 11/1976 | Parker | 250/574 X |
| 4,043,669 | 8/1977 | Gehatia et al. | 356/246 X |
| 4,504,396 | 3/1985 | Vardi et al. | 95/260 X |
| 4,842,406 | 6/1989 | VonBargen | 356/336 |
| 4,872,353 | 10/1989 | Orr, Jr. et al. | 73/864.85 |
| 4,920,550 | 4/1990 | Olivier et al. | 356/246 X |
| 5,439,288 | 8/1995 | Hoffman et al. | 366/127 X |
| 5,575,913 | 11/1996 | Sharkey | 210/409 |
| 5,576,827 | 11/1996 | Strickland et al. | 356/336 |

FOREIGN PATENT DOCUMENTS

| | | | |
|---|---|---|---|
| 1189458 | 6/1985 | Canada | 95/30 |
| 256419 | 5/1988 | Germany | 95/30 |
| 2-26602 | 1/1990 | Japan | 96/204 |

OTHER PUBLICATIONS

"Microtrac® Asvr Automated Small Volume Recirculator," copy of page from Leeds & Northrup Wales, PA, © 1993.
"Horiba Laser Scattering Particle Size Distribution Analyzer LA–910," copy of catalog page, Horiba, Ltd. Head Office, Kyoto, Japan, Bulletin HRE–3630, Undated.
"Laser Diffraction Particle Size Analyzer SALD–2001," copy of catalog page, Shimadzu Corporation, Tokyo, Japan, Undated.
"SympaTEC, System–Partikel–Technik," analytical software, technical specifications, copy of brochure page, 1993.
"Micromeritics Sedigraph 5000D Particle Size Analyzer," Brochure, by Micromeritics Instrument Corporation, pp. 00414–00421, Undated.
"Microscan Particle Size Analyzer," brochure by Quantachome Corporation, Jun., 1986.
"Instruction Manual Sedigraph 5000ET. Particle Size Analyzer,"by Micromeritrics Instrument Corporation, Jan. 15, 1986.

*Primary Examiner*—Richard L. Chiesa
*Attorney, Agent, or Firm*—Jones & Askew, LLP

[57] ABSTRACT

A sample handling system provides an evenly-suspended, small volume, bubble-free sample to an analyzer such as a light scattering particle size analyzer. A flow of suspension is forced through an elongate channel below the surface of the liquid in the channel, along a downwardly sloping path, into impact with an end wall, and through an abrupt downward turn. Controlled turbulence created in the flow disperses particles and releases bubbles from the liquid.

15 Claims, 5 Drawing Sheets

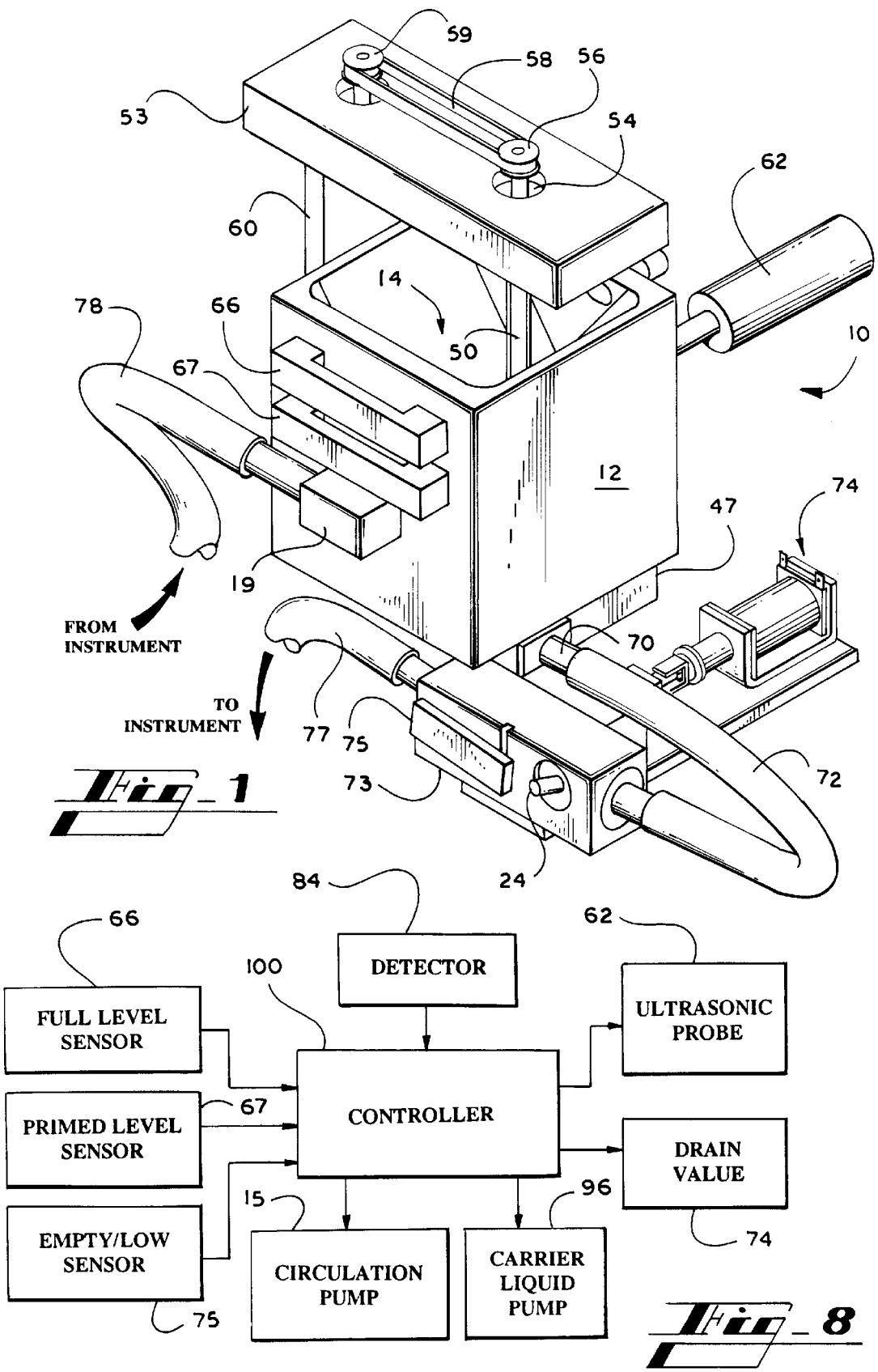

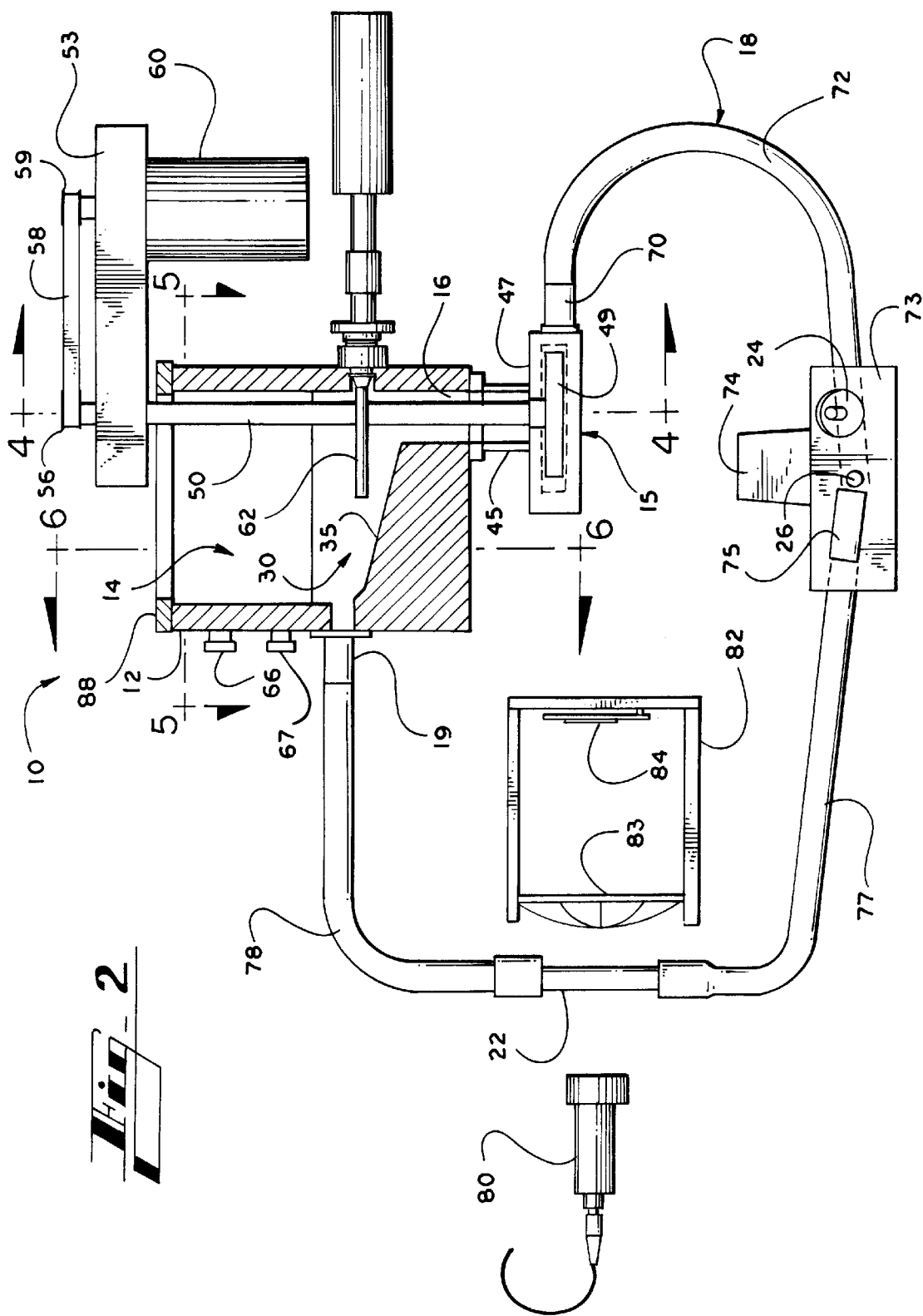

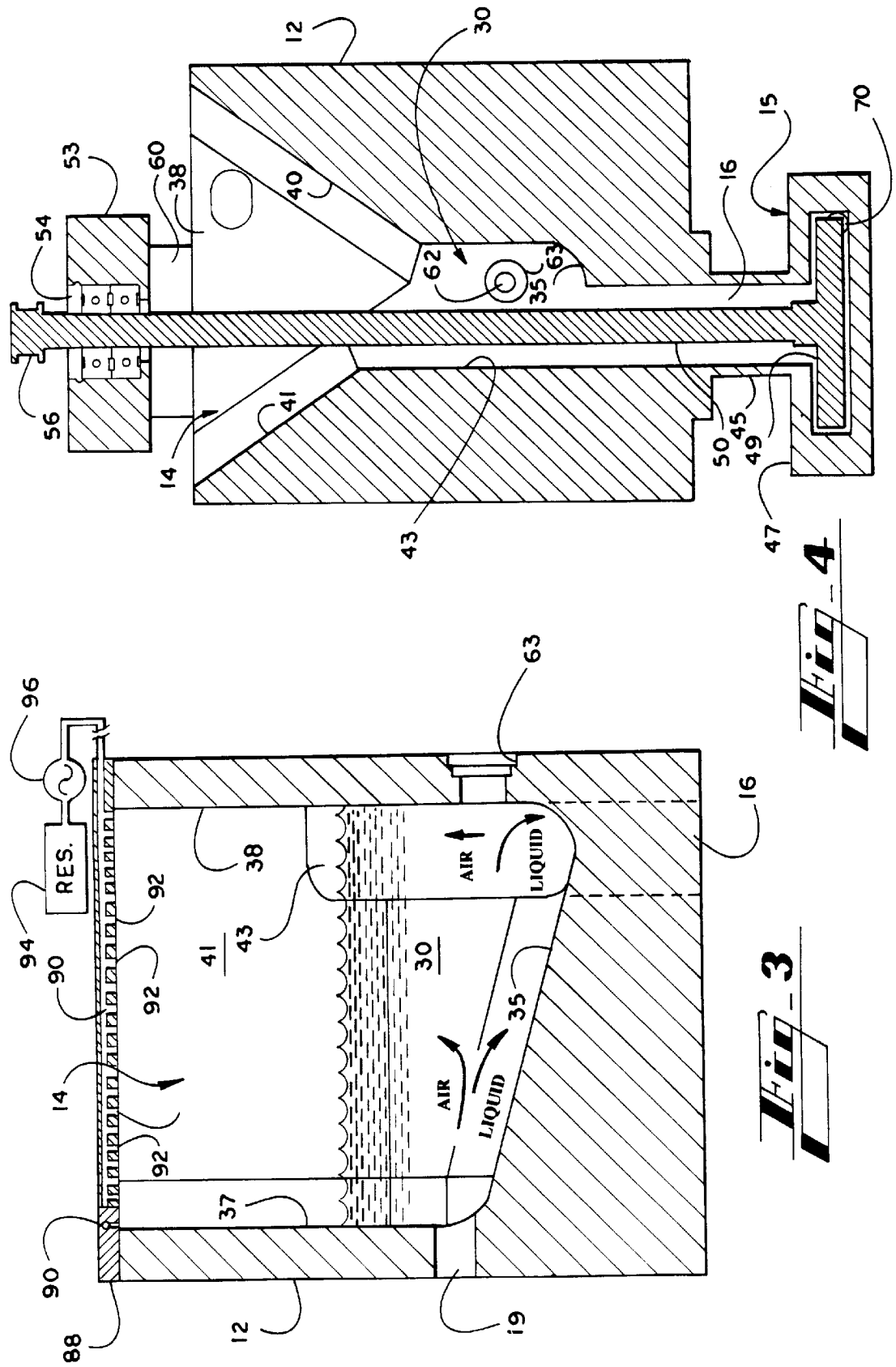

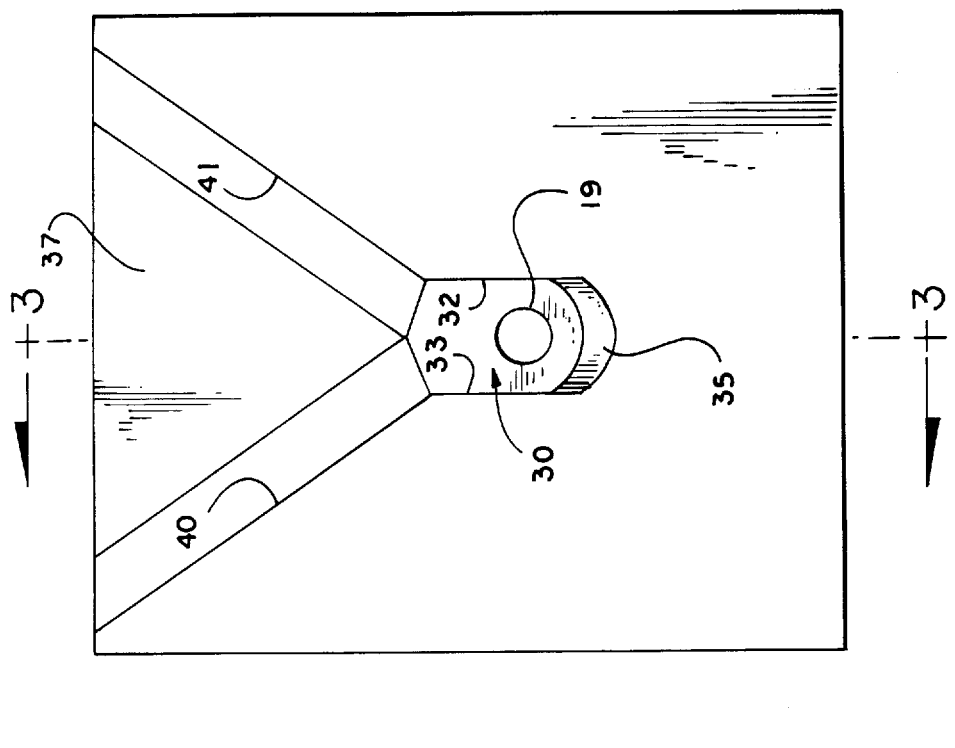
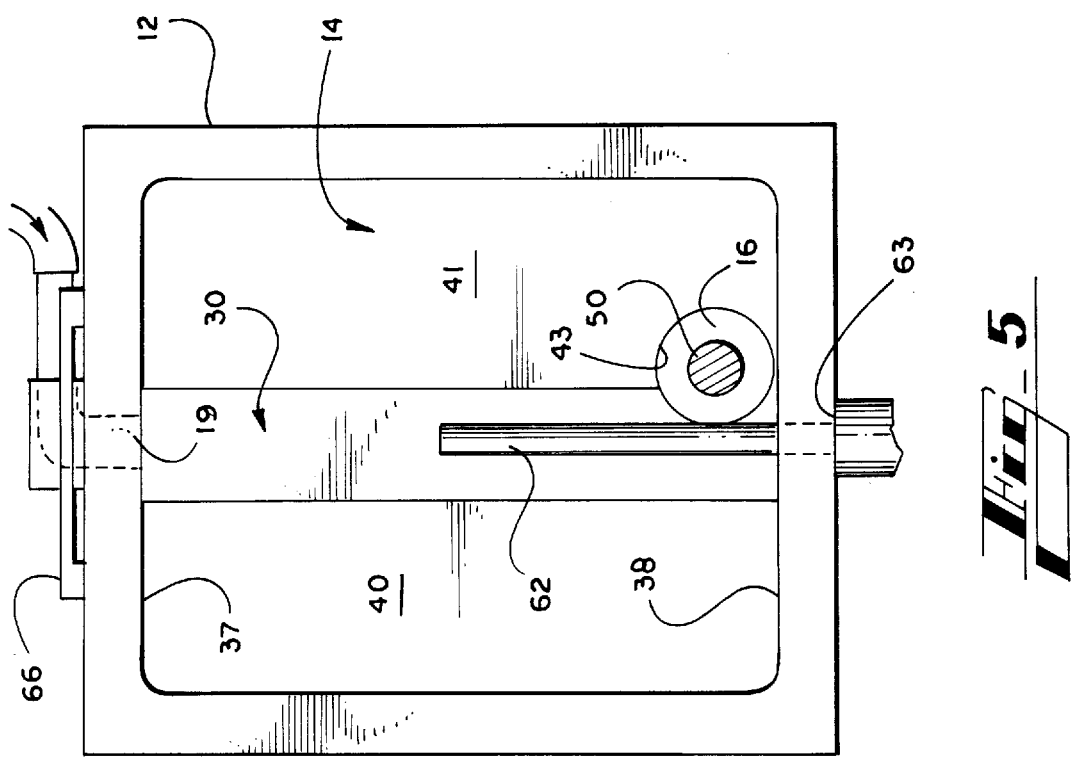

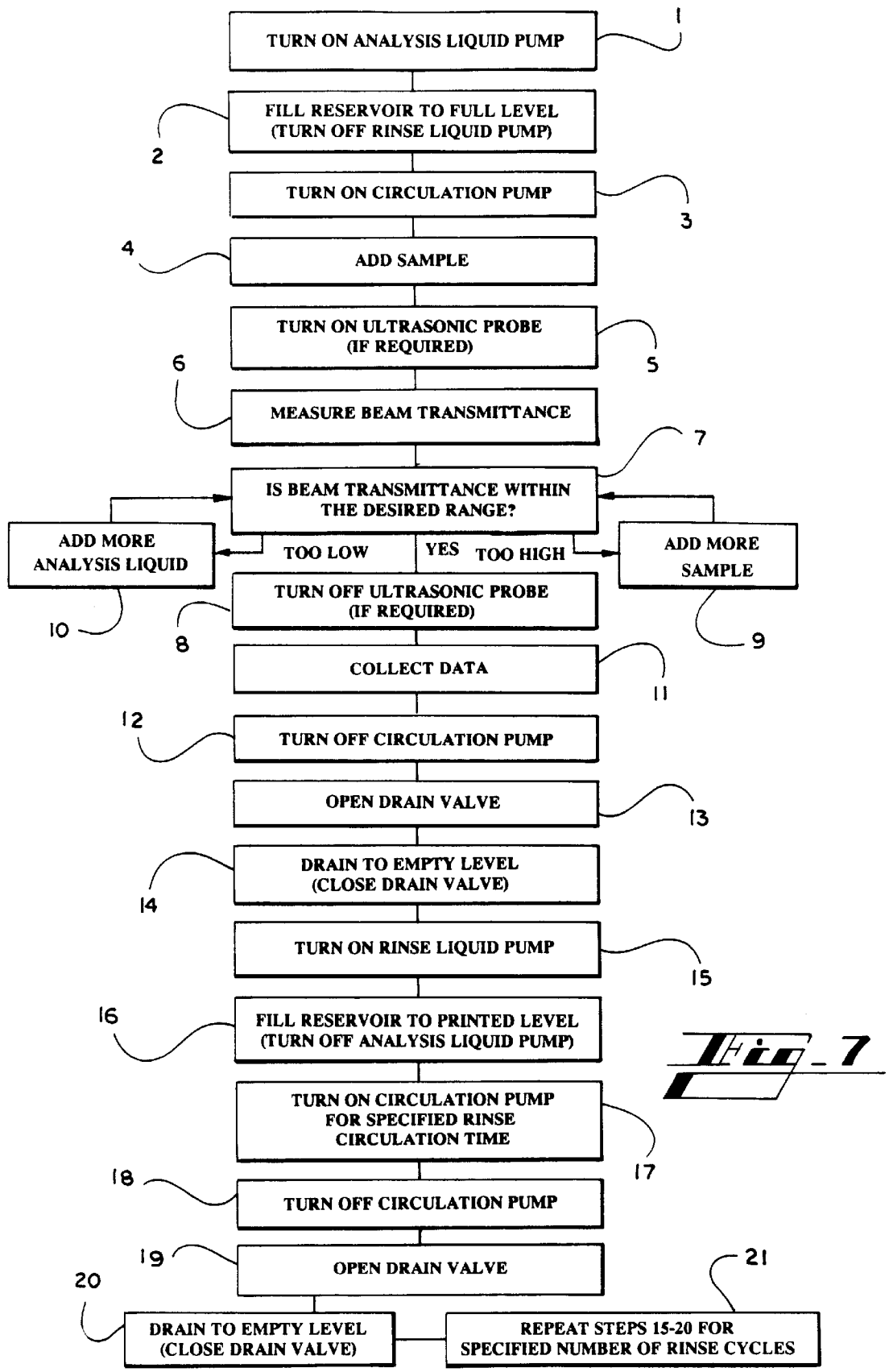
Fig_7

SYSTEM AND METHOD FOR EVENLY SUSPENDING AND CIRCULATING PARTICLES IN A LIQUID

TECHNICAL FIELD

The present invention relates to methods and systems for suspending particles in liquids, and more particularly to a method and system for providing an evenly-suspended, small volume, bubble-free sample to an analyzer such as a light scattering particle size analyzer.

BACKGROUND OF RELATED ART

In science and industry, various instruments often work on suspensions of particles in a liquid carrier medium, also referred to as the analysis liquid. To produce accurate results, the sample suspension must be evenly dispersed within the carrier liquid, and the suspension must be free of bubbles. Often there is a need for small volume samples on the order of 300 cc or less, suspended in a lower viscosity liquid, such as water. An example of such an analyzer is the light scattering particle size analyzer described in U.S. Pat. No. 5,576,827, which is incorporated herein by reference in its entirety. Analyzers of this type require recirculation of a sample suspension continuously through a sample analysis cell at a high flow rate. The upward velocity of the flow should exceed the settling velocity of all the particles in the suspension, to achieve near equal time of exposure in the light beam of all particles. If large particles in the suspension are allowed to settle under the influence of gravity, this may distort the resulting particle size distribution.

In other situations there may be a need for a one-time delivery of an evenly-suspended, bubble-free sample.

Current systems for handling suspended samples typically use stirrers or injection flow to create a cylindrical vortex in a reservoir to disperse the particles. These systems create excess turbulence, entrapping air in the process. Air may also enter the system during circulation or in the filling process. The air must be removed in a bubble elimination routine where the flow rate is slowed to allow bubbles to rise and vent to atmosphere. However, to keep heavier particles evenly dispersed in a small volume of a suspension, a high flow rate must be maintained. The compromises made in current systems, to balance the competing goals of minimizing bubbles and maximizing dispersion, have resulted in less precise analytical results.

SUMMARY OF THE INVENTION

The present invention seeks to provide an improved system and method for providing an evenly-dispersed, bubble-free suspension of particles in a small volume of liquid.

In accordance with the invention, this object is accomplished by creating controlled turbulence in a reservoir to disperse particles in a small volume of liquid without entrapping air bubbles in the liquid. The method and system according to the invention direct a suspension of the particles in the liquid along a sloping channel ending in a turn below the surface of the liquid, resulting in minimal disturbance of the momentum of the liquid with controlled turbulence. No air is entrapped at the surface, and the suspension is de-aerated.

Generally described, the present invention provides a method and system for transferring a suspension including a liquid containing suspended particles by injecting a flow of the suspension into a reservoir of the suspension at an inlet location below a surface of the suspension in the reservoir; directing the flow of suspension in a downwardly sloping path across the reservoir and through a turn; and withdrawing the suspension from the reservoir through an outlet positioned in a lower surface of the reservoir. In a preferred embodiment, the system forces a flow of the suspension along a channel formed in a bottom portion of the reservoir into an impact wall of the reservoir opposite the inlet location, and then through a 45–90 degree turn down along the impact wall to the outlet. In a recirculating embodiment, the flow of suspension travels from the outlet through a circulating pathway to the inlet location.

A sample handling system and method in accordance with the invention has a number of advantages. It can accept samples having a small volume of 300 cc or less in the reservoir, direct the sample suspension through the circulating pathway at a rate of 200 cc/sec or faster, create controlled turbulence in the suspension in the reservoir without entrapping significant air bubbles, maintain the particles approximately evenly in suspension, and release bubbles from the suspension within the reservoir. As a result, small volume samples can be analyzed while homogeneously dispersed, without the aid of a mechanical stirrer, and without interference from bubbles.

A system and method in accordance with the invention de-aerates the suspension because bubbles rise as the flow travels downwardly along the relatively long sloping path, and then more bubbles are released on impact of the flow with the reservoir wall. This de-aeration is effective even though the flow rate of the suspension through the reservoir is not decreased.

In a preferred embodiment, an ultrasonic probe extends from the impact wall of the reservoir into the flow channel, to assist in dispersing clumps of particles present in the suspension. A non-pulsatile pump preferably is positioned at the outlet of the reservoir, and preferably comprises an impeller in a volute formed below the outlet, with the impeller drive shaft extending up through the outlet and through the reservoir to a drive assembly above. The walls of the reservoir above the channel preferably are sloped upwardly and outwardly, to ensure that particles cannot settle from the liquid without being swept from the reservoir surfaces by the passage of liquid.

According to other aspects, the present invention provides a system and method for de-bubbling a liquid, for uniformly suspending and de-bubbling a suspension of particles in a liquid, and for providing a recirculating sample source for a scientific or industrial analyzer of suspended particles.

Other objects, features, and advantages of the present invention will become apparent upon review of the following detailed description of preferred embodiments thereof, when taken in conjunction with the appended drawings.

BRIEF DESCRIPTION OF THE DRAWINGS

FIG. 1 is a pictorial view of a sample handling system according to the present invention.

FIG. 2 is a schematic view of the components of the sample handling system of FIG. 1.

FIG. 3 is a side cross sectional view of the reservoir of the sample handling system of FIG. 1, taken along line 3—3 of FIG. 6.

FIG. 4 is an end cross sectional view of the reservoir of the sample handling system of FIG. 1, taken along line 4—4 of FIG. 2, looking toward the outlet end of the reservoir.

FIG. 5 is a top view taken along line 5—5 of FIG. 2.

FIG. 6 is an end cross sectional view of the reservoir of the sample handling system of FIG. 1, taken along line 6—6 of FIG. 2, looking toward the inlet end of the reservoir.

FIG. 7 is a flow diagram of the sequence of operation of the sample handling system.

FIG. 8 is a block diagram representing the control circuit of the sample handling system.

DETAILED DESCRIPTION OF THE INVENTION

Referring now to the drawings, in which like numerals represent like parts throughout the several views, FIG. 1 shows a sample handling system 10 embodying the present invention, for providing an evenly-suspended, small volume, bubble-free suspension of a particulate sample in a carrier liquid. The sample handling system 10 generally includes a reservoir 12 defining a liquid containing cavity 14, a circulation pump 15 connected to an outlet of the reservoir 12, and a recirculation passageway 18 leading from the outlet 16 to a reservoir inlet 19. A sample inlet port 24 for introducing particulate sample into the system is provided in the passageway 18, as is a drain 26 for emptying the system.

The shape of the cavity 14, described in detail below, is designed to create controlled turbulence so as to keep particles suspended without entrapping air in the suspension. As shown diagrammatically in FIG. 2, the evenly dispersed sample may be delivered to a sample analysis cell 22 of an analyzer such as a light scattering particle size analyzer.

The reservoir preferably is formed from a dense plastic material such as chemical resistant high density polyethylene (HDPE) or ultra high molecular weight polyethylene (UHMWPE). Other non-reactive plastics or metals can be used. The shape of the cavity 14 may be seen from examination of FIGS. 2–6. A relatively narrow channel 30 is formed at the bottom of the cavity. The channel 30 has a pair of vertical side walls 32 and 33 connected by a bottom surface 35. The channel extends from a vertical inlet end wall 37 of the cavity 14 to a vertical outlet end wall 38. As best shown in FIG. 6, the inlet 19 passes through the inlet end wall 37 within the channel 30. The bottom surface 35 slopes downwardly from the inlet wall to the outlet wall. A pair of cavity walls 40 and 41 slope upwardly from the channel side walls 33 and 32, respectively, to form a further liquid holding volume above the channel. Liquid exits at the lowest point of the channel through the outlet 16.

At the outlet wall 38, an enlarged vertical passageway 43 is cut into the wall 41 and the bottom surface 35, leading down to the outlet 16. As best shown in FIG. 4, a hollow neck 45 connects the outlet 16 to the pump 15. A pump volute 47 positioned at the end of the neck 45 contains an impeller 49 of the pump. An impeller drive shaft 50 attached to the impeller extends up through the passageway 43 and the cavity 14 and is overhung from an impeller support block 53 above the reservoir 12. The drive shaft 50 is captured in a bearing 54 positioned in the block 53. Referring to FIGS. 1 and 2, a pulley 56 is fitted on the drive shaft above the bearing 54. The drive shaft 50 is rotated by a timing belt 58 that passes around the pulley 56 and is driven by a pulley 59 connected to the drive shaft of a pump motor 60 carried below the support block 53.

The passageway 43 and the outlet 16 are off center with respect to the channel 30, as shown in FIGS. 4 and 5. This positions the shaft 50 to the side of the channel, leaving a linear flow path within the channel from the inlet 19 to the outlet end wall 38. It should be noted that the positioning of the impeller drive shaft obviates the need for any rotating shaft seals that could deteriorate in the presence of abrasive particles in the suspension. A non-pulsatile pump is used because a smooth flow through the sample cell 22 is required. A diaphragm pump could be used, but the impeller pump is preferred because the seals of a diaphragm pump are subject to wear when pumping a particulate suspension.

An ultrasonic probe 62 extends through the outlet end wall 38 at a fitting 63 and horizontally into the channel 30. The probe 62 assists in breaking up any clumps of particles and dispersing the particles within the suspension in a well known manner.

Two level sensors are positioned on the reservoir 12 to sense the presence or absence of liquid in the cavity 14. A "full" level sensor 66 is spaced a short distance below the top of the reservoir, and "primed" level sensor 67 is spaced about 5–7 mm above the inlet 19. Both of the sensors 66 and 67 are ultrasonic level detectors, of a well known type sometimes used as bubble detectors, mounted on the exterior of the reservoir 12. The level sensors detect the presence or absence of liquid in the cavity through the plastic walls of the reservoir. The full level sensor preferably is positioned to indicate a system volume of 650 cc. The primed level sensor is positioned to indicate a system volume of 300 cc, of which about 150 cc is normally in the reservoir.

No precise size and shape for the channel 30 is critical so long as a flow can be established as described below. The sloping cavity walls 40 and 41 are not critical to the flow characteristics established in the channel, but they help to assure that the reservoir drains completely. It would be possible to construct a channel-shaped reservoir according to the invention without an enlarged volume above the channel. The optimum size and shape of the channel will vary according to the volume of the sample suspension. For a suspension of 300 cc or less, the channel 30 preferably is about 11.4 cm long from end wall 37 to end wall 38, about 2 cm deep at the inlet end wall 37, about 4.2 cm deep at the outlet wall 38, and about 1.2–2.5 cm wide. The slope of the bottom surface 35 should be in a range from 15–30 degrees, preferably about 20 degrees for optimum de-aeration.

The impeller 49 pumps liquid through a pump outlet 70 into the recirculation passageway 18. A tubing section 72 connects the pump outlet 70 to a drain and fill manifold 73 positioned at the lowest level of the system 10. The analysis sample inlet 24 is located in the manifold 73, as is a drain valve assembly 74 which is operative to open and close the drain outlet 26. Also contained within the manifold 73 is an "empty/low" level sensor that detects when the system is empty of liquid. The manifold 73 is connected to the sample cell 22 of the associated instrument by tubing section 77, and the sample cell 22 is connected to the reservoir inlet 19 by a tubing section 78 to complete the recirculation passageway 18.

The instrument to which the suspension is supplied is of the type requiring an evenly dispersed suspension of particles in the carrier liquid, such as a light scattering particle size analyzer. Such an instrument is disclosed in the above-mentioned U.S. Pat. No. 5,576,827. The suspension is subjected to a beam of light from a light source 80. Light scattered by the suspension enters a camera 82 where it is focused by a lens 83 onto a detector 84, in a manner further described in the patent.

The sampling handling system 10 is equipped with a shower fixture 88 for rinsing the cavity 14 of the reservoir 12, or for filling the cavity with carrier liquid. The fixture is shown in FIGS. 2 and 3, but is removed in FIG. 1. The fixture 88 is a rectangular plate formed of plastic or metal that is non-reactive with the carrier liquids to be used in the system. A liquid conduit 90 is formed within the plate extending around its four sides, one of which is shown in FIG. 3. From the conduit, a plurality of spaced apart spray outlets or nozzles extend downwardly to open at the bottom of the plate adjacent to the walls 37, 38, 40, and 41 of the cavity 14. Clear carrier liquid from a liquid reservoir 94 is pumped via a pump 96 into the conduit 90 and out of the spray outlets 92. This provides an even spray shower of rinsing liquid all around the cavity walls from the top down. Any particulate or a previous carrier liquid adhering to the walls is rinsed down into the channel, out through the outlet 16 and down to the drain outlet 26.

Automated operation of the sampling handling system 10 is provided using a controller 100 that is connected to various components of the system in the manner shown in FIG. 8. The controller may be a personal computer equipped with a standard interface for exporting data and control signals to the other devices shown in FIG. 8, and programmed to carry out the functions and steps described below in connection with FIG. 7. Such programming is within the capabilities of a programmer of ordinary skill. The sampling handling system 10 may be controlled by the same computer that controls the analyzer of which the sample cell 22 is a part. Alternately, the controller could be another form of general purpose microprocessor or a programmed logic controller (PLC). The pumps and valves could also be operated manually.

The controller 100 is connected to receive status information from the level sensors 66, 67, and 75, and output signals from the detector 84. It is also connected to send control signals to the circulation pump 15, the carrier liquid pump 96, the ultrasonic probe 62, and the drain valve 74. Those skilled in the art will understand that it would be possible to connect the sample inlet 24 to an automatic sample feeder (not shown), for example of the type shown in U.S. Pat. No. 4,872,353, which is incorporated herein by reference in its entirety. In this case the controller would be connected to send command signals to the sample feeder, and to receive appropriate status inputs.

Operation of the sampling handling system 10 in association with a light scattering particle size analyzer preferably proceeds according to the steps outlined in the flow chart of FIG. 7. Initially, the carrier or analysis liquid pump 96 is operated (block 1) by the controller 100 to fill the recirculation passageway 18 and the cavity 14 from the liquid reservoir 94 up to the level of the primed level sensor 67 (preferably about 300 cc), and then the pump 96 is stopped (block 2). Then the circulation pump 15 is operated (block 3) to circulate the liquid through the system. The sample to be analyzed, usually a concentrated suspension of particles, is manually or automatically injected into the sample inlet port 24 (block 4), and the ultrasonic probe 62 is activated (block 5) if needed to thoroughly break up and disperse the particulate sample. The particles traveling along the channel come into intimate contact with the tip of the ultrasonic probe on every recirculating pass through the channel.

After a newly loaded sample has been recirculated and dispersed by the system 10, the controller 100 checks the output from the detector 84 (block 6) to determine whether the transmittance of light from the light source 80 through the sample cell 22 is within a predetermined desired range that was previously stored in the memory of the controller (block 7). If the transmittance is too high, the controller prompts the operator to add more sample (block 9). If the transmittance is too low, the controller operates the pump 96 to add more carrier liquid to the reservoir 12 (block 10). After the step of block 9 or block 10, the logic returns to block 7 to re-test the transmittance.

When the transmittance tests within the desired range, the ultrasonic probe 62 is turned off, if it was used (block 8). Then the circulation of the suspension through the sample cell 22 and the reservoir 12 continues while data is collected by the detector 84 (block 11) in accordance with the operation of the particle size analyzer. After completion of data collection, the circulation pump 15 is turned off (block 12), and the drain valve 74 is opened (block 13) to allow the suspension to drain through the drain outlet 26. When the empty level sensor 75 detects an absence of liquid in the system, the drain valve 74 is closed (block 14). Then the carrier liquid pump 96 is operated to spray liquid through the shower fixture 88 to rinse the walls of the cavity 14 (block 15) until the liquid level rises to the full level sensor 66 (block 16) at which time the pump 96 is turned off. The circulation pump 15 then is operated for a predetermined rinse circulation time (block 17), after which the pump 15 is turned off (block 18). The drain valve 26 is opened (block 19) until the empty level sensor 75 detects no liquid (block 20).

The steps of blocks 15 to 20 then may be repeated a predetermined number of times to fully rinse the previous sample from the system. It should be understood that the parameters identified above as predetermined can be user-defined, and adjusted by a system operator to meet particular needs.

An important aspect of a sample handling system 10 according to the present invention is the ability of the system to provide an evenly-dispersed, bubble-free suspension of particles in a small volume of liquid. The flow of liquid from the inlet 19 through the channel 30 creates controlled turbulence that mixes the suspension and disperses the particles of the suspension without entrapping air bubbles in the liquid. The pump 15 preferably pulls the suspension through the channel 30 at a rate of about 200 cc/sec. The pull of the pump causes the liquid to follow a relatively linear, downwardly sloping path from the inlet 19 across to the end wall 38 of the reservoir. Here, the liquid is forced to turn abruptly down toward the outlet 16.

Turbulence is created in the liquid flow as the rapid flow impacts the end wall and turns down. This turbulence agitates the suspension and mixes the particles homogeneously therein, without the aid of a mechanical stirrer. Furthermore, the rapid speed of the flow tends to hold the particles in suspension. However, the turbulence occurs substantially below the surface of the liquid, as does the abrupt turn of the flow. Thus, no swirling vortex is formed that would suck air into the liquid, and any turbulence created at the liquid surface is insufficient to entrap any significant air in the liquid.

As the liquid flow moves from the inlet 19, it is pulled down along the sloping bottom surface 35 of the channel 30. Bubbles previously incorporated in the liquid, such as during the filling process, tend to rise as the flow goes downward, as indicated in FIG. 3. The length of the channel gives some bubbles time to escape to the surface. Then, when the flow impacts the end wall 38, the momentum of any remaining bubbles is disrupted, and they are able to escape the flow and rise. Some circulation of liquid around the drive shaft 50 may occur. These features enable the system 10 to de-aerate the liquid even at flow rates up to 200 cc/sec. Thus, the flow need not be slowed for a de-bubbling routine, which would allow particles to settle. There are no regions in the circulatory path of sufficiently low flow for particles to collect and effectively be removed from the sample.

The shape of the channel 30 allows these results to be achieved with a small liquid volume of 300 cc or less, which is not possible using prior sample handling systems, unless the flow rate is reduced well below 200 cc/sec and some means for mixing and maintaining particle dispersion is provided.

It should be understood that a reservoir according to the present invention can be used for purposes other than to maintain a recirculating suspension. For example, a suspension could be run through the channel 30 and pump 15 to increase flow velocity, increase the dispersion of particulate, remove bubbles, or all three functions. The apparatus could also be used to de-aerate clear liquid.

While this invention has been described in detail with particular reference to a preferred embodiment thereof, it will be understood that modifications and variations may be made without departing from the scope of the invention as defined in the appended claims.

What is claimed is:

1. An apparatus for transferring a suspension including a liquid containing dispersed particles, comprising:
   a reservoir defining an elongate channel having substantially vertical side walls along the bottom thereof and defining an upper portion including upper side walls sloping upwardly and outwardly from opposite side walls of said channel, said suspension defining an upper surface within said reservoir;
   an inlet positioned to inject said suspension laterally into said reservoir along said channel along a flow path below said upper surface of said suspension;
   an outlet positioned in said channel spaced from and below said inlet, said channel including a lower surface sloping downwardly from said inlet to said outlet and extending from a first end wall of said reservoir in which said inlet is positioned, to a second end wall of said reservoir against which said flow path impinges above said outlet, said flow path sloping downwardly from said inlet to said second end wall, and turning abruptly downwardly to said outlet;
   a circulating fluid pathway connecting said inlet to said outlet outside said reservoir: and
   a non-pulsatile pump positioned in said circulating fluid pathway to pull said suspension from said outlet.

2. The apparatus of claim 1, further comprising an ultrasonic probe extending into said channel from said second end wall.

3. The apparatus of claim 1, wherein said pump comprises an impeller within a volute, and an impeller drive shaft extending from said impeller up through said outlet and said suspension in said reservoir.

4. An apparatus for uniformly suspending and de-bubbling a suspension of particles in a liquid, comprising:
   a reservoir, including:
      an elongate channel having substantially vertical side walls along the bottom of said reservoir, extending from a first end wall of said reservoir to a second end wall of said reservoir, said channel including a lower surface sloping downwardly from said first end wall to said second end wall;
      an upper portion including upper side walls sloping upwardly and outwardly from opposite side walls of said channel, said suspension filling said channel and said upper portion to an upper surface of said suspension;
      an inlet positioned in said first end wall to inject said suspension laterally into and along said channel along a flow path extending from said inlet to said second end wall;
      an outlet positioned in said lower surface of said channel adjacent to said second end wall;
      a circulating fluid pathway connecting said inlet to said outlet outside said reservoir: and
      a non-pulsatile pump positioned in said circulating fluid pathway to pull said suspension from said outlet and to move said suspension along said flow path at a velocity sufficient to maintain said particles in suspension in said liquid and to impinge a flow of said suspension against said second end wall and turn abruptly downwardly to said outlet,
      whereby controlled turbulence is created in said suspension in said reservoir without entrapping significant air bubbles, said particles are maintained approximately evenly in suspension, and bubbles are released from said suspension within said reservoir.

5. The apparatus of claim 4, wherein said flow of suspension is at least 200 cc/sec.

6. The apparatus of claim 4, wherein said flow of suspension travels at a speed of at least 1 meter/sec.

7. The apparatus of claim 4, wherein said non-pulsatile pump comprises an impeller within a volute below said outlet, and an impeller drive shaft extending from said impeller up through said outlet and said suspension in said reservoir.

8. The apparatus of claim 4, further comprising an ultrasonic probe extending into said channel from said second end wall.

9. The apparatus of claim 4, further comprising a spray fixture mounted above said reservoir and including spray outlets for directing a spray of liquid down the side walls and end walls of said reservoir.

10. A method of transferring a suspension including a liquid containing suspended particles, comprising the steps of:
    injecting a flow of said suspension into a reservoir of said suspension at an inlet location below a surface of said suspension in said reservoir;
    directing said flow of suspension, in a path sloping downwardly along a channel having substantially vertical side walls formed in a bottom portion of said reservoir positioned below an upper portion of said reservoir including upper side walls sloping upwardly and outwardly from opposite side walls of said channel, into an impact wall of said reservoir opposite said inlet location, and then turning abruptly downwardly along said impact wall to an outlet;
    withdrawing said suspension with said particles dispersed in said liquid from said reservoir through said outlet positioned in a lower surface of said reservoir; and
    directing said flow of suspension with a non-pulsatile pump from said outlet through a circulating pathway to said inlet location.

11. The method of claim 10, further comprising the step of dispersing said suspension with an ultrasonic probe extending into said reservoir from said impact wall.

12. The method of claim 10, wherein said method comprises placing 300 cc or less of said suspension in said reservoir to a level above said inlet location, and directing said suspension through said circulating pathway at a rate of at least 200 cc/sec.

13. The method of claim 10, whereby said steps create controlled turbulence in said suspension in said reservoir without entrapping significant air bubbles, maintain said particles approximately evenly in suspension, and release bubbles from said suspension within said reservoir.

14. The method of claim 10, wherein said step of directing said flow of suspension in a downwardly sloping path across said reservoir into an impact wall of said reservoir opposite said inlet location, and then down along said impact wall, includes creating turbulence beneath the surface of said suspension, while creating insufficient turbulence at the surface to entrap air into the liquid.

15. An apparatus for uniformly suspending and de-bubbling a suspension of particles in a liquid, comprising:

a reservoir, including:

an elongate channel along the bottom of said reservoir, extending from a first end wall of said reservoir to a second end wall of said reservoir, said channel including a lower surface sloping downwardly from said first end wall to said second end wall;

an upper portion including side walls sloping upwardly and outwardly from opposite sides of said channel, said suspension filling said channel and said upper portion to an upper surface of said suspension;

an inlet positioned in said first end wall to inject said suspension laterally into and along said channel along a flow path extending from said inlet to said second end wall;

an outlet positioned in said lower surface of said channel adjacent to said second end wall;

a circulating fluid pathway connecting said inlet to said outlet outside said reservoir;

a non-pulsatile pump comprising an impeller within a volute below said outlet, and an impeller drive shaft extending from said impeller up through said outlet and said suspension in said reservoir, said pump being positioned in said circulating fluid pathway to pull said suspension from said outlet for moving said suspension along said flow path at a velocity sufficient to maintain said particles in suspension in said liquid and to impinge a flow of said suspension against said second side wall; and an ultrasonic probe extending into said channel from said second end wall;

whereby controlled turbulence is created in said suspension in said reservoir without entrapping significant air bubbles, said particles are maintained approximately evenly in suspension, and bubbles are released from said suspension within said reservoir.

* * * * *

US005849064B1

REEXAMINATION CERTIFICATE (4079th)

United States Patent [19]
Marco et al.

[11] B1 5,849,064
[45] Certificate Issued May 2, 2000

[54] SYSTEM AND METHOD FOR EVENLY SUSPENDING AND CIRCULATING PARTICLES IN A LIQUID

[75] Inventors: William P. Marco, Norcross; John M. Ward, Grayson; James P. Olivier, Lawrenceville; Preston P. Hendrix, Hoschton, all of Ga.

[73] Assignee: Micromeritics Instrument Corporation, Norcross, Ga.

Reexamination Request:
No. 90/005,477, Sep. 7, 1999

Reexamination Certificate for:
Patent No.: 5,849,064
Issued: Dec. 15, 1998
Appl. No.: 08/839,502
Filed: Apr. 14, 1997

[51] Int. Cl.⁷ .................................................. B01D 19/00
[52] U.S. Cl. .................................. 95/30; 95/260; 95/262; 96/175; 96/204; 96/220; 96/389
[58] Field of Search .............................. 95/30, 260, 262; 96/175, 204, 220, 389, 206, 228, FOR 132; 210/533–535, 539, 409

[56] References Cited

U.S. PATENT DOCUMENTS

| | | | |
|---|---|---|---|
| 3,908,465 | 9/1975 | Bartlett | 73/865.5 |
| 4,298,357 | 11/1981 | Pernic | 96/174 |
| 5,324,166 | 6/1994 | Elonen et al. | 415/169.1 |
| 5,475,486 | 12/1995 | Paoli | 356/246 |

FOREIGN PATENT DOCUMENTS

| | | |
|---|---|---|
| 6-316886 | 11/1994 | Japan . |
| WO 88/02855 | 4/1988 | WIPO . |
| WO 95/28630 | 10/1995 | WIPO . |

*Primary Examiner*—Richard L. Chiesa

[57] ABSTRACT

A sample handling system provides an evenly-suspended, small volume, bubble-free sample to an analyzer such as a light scattering particle size analyzer. A flow of suspension is forced through an elongate channel below the surface of the liquid in the channel, along a downwardly sloping path, into impact with an end wall, and through an abrupt downward turn. Controlled turbulence created in the flow disperses particles and releases bubbles from the liquid.

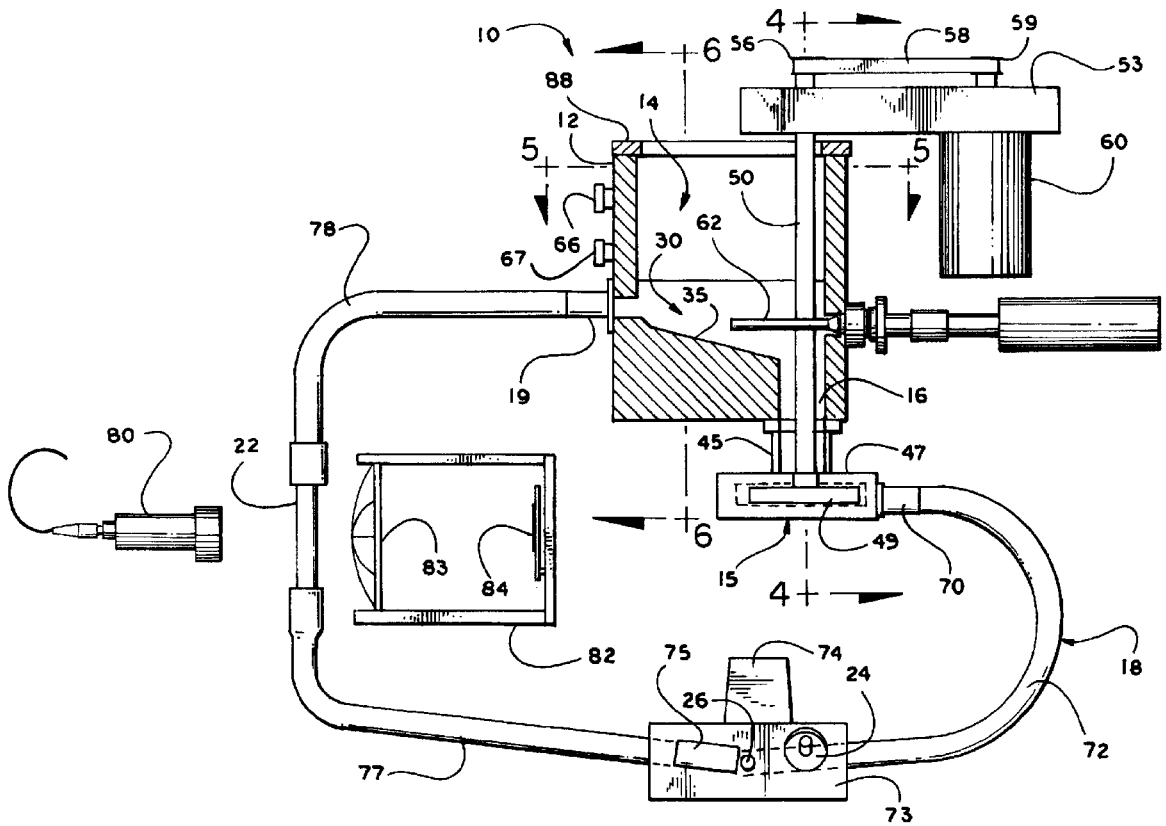

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *